Feb. 17, 1953 E. S. BOERNER Plant Pat. 1,168
CHRYSANTHEMUM PLANT
Filed April 29, 1952
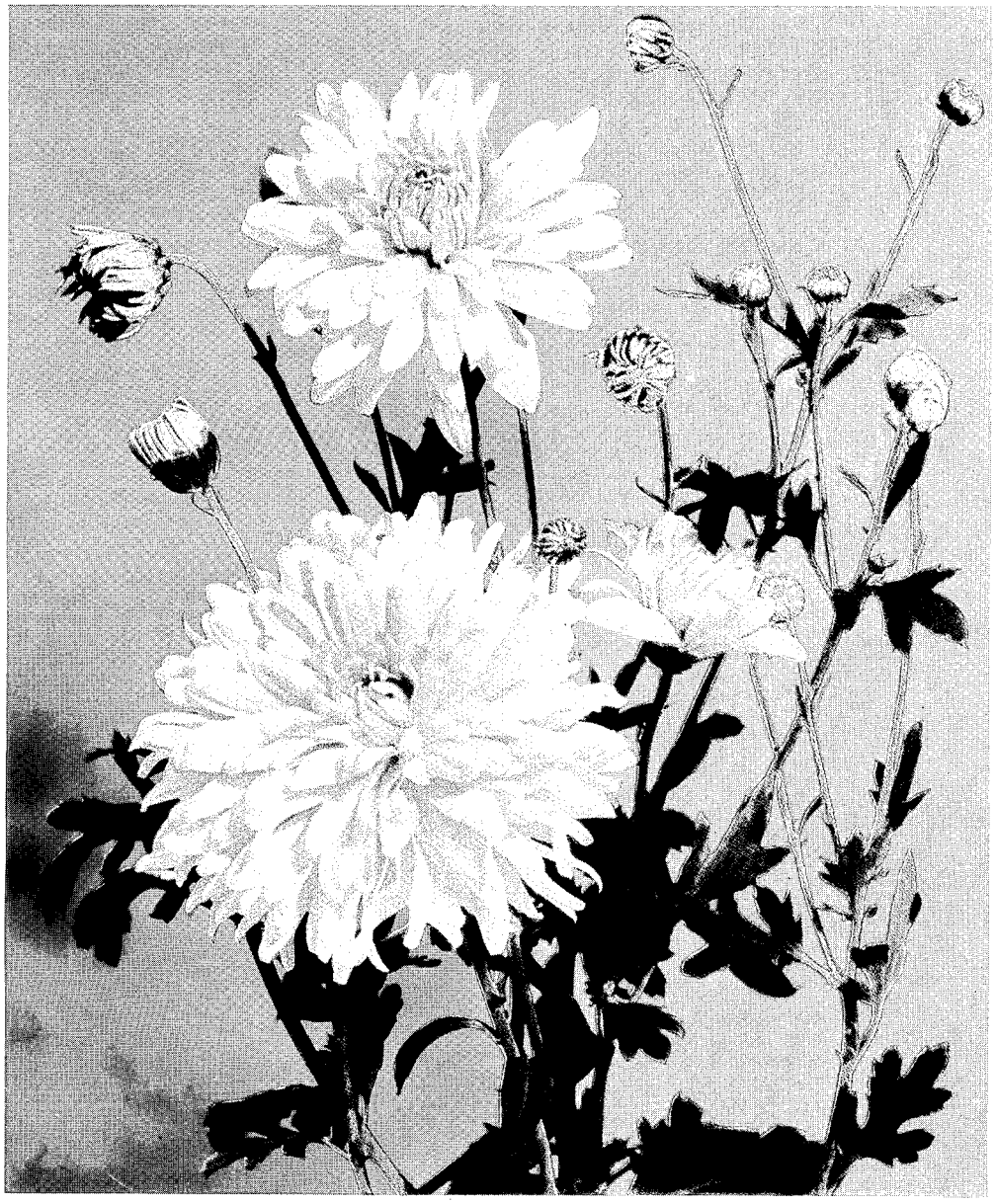
Inventor.
E. S. Boerner
By: Robb & Robb
Attorneys.

Patented Feb. 17, 1953

Plant Pat. 1,168

UNITED STATES PATENT OFFICE 1,168

CHRYSANTHEMUM PLANT

Eugene S. Boerner, Newark, N. Y., assignor to Jackson & Perkins Company, Newark, N. Y., a corporation of New York Application April 29, 1952, Serial No. 284,923

1 Claim. (Cl. 47—60)

The present invention relates to a new and distinct variety of chrysanthemum plant of the decorative type that was originated by me by crossing an unnamed and unpatented seedling of "Nita" with an unnamed and unpatented seedling derived by crossing the unpatented variety "Mrs. Dupont" by another unnamed and unpatented seedling.

The primary objective of this breeding was to produce a new variety of chrysanthemum which bears blooms of the color of the variety "Mrs. Dupont," but which is endowed with the characteristics of healthier growth, better form and more frost resistance.

This objective was substantially obtained, as evidenced by the fact that my new variety is more upright than the variety "Mrs. Dupont," its stems are stiff and hold up well, its blooms are of the decorative type and are very freely produced, and its foliage has a silvery cast over the entire plant and which is easily recognized and makes it distinctive from any other variety, these characteristics altogether constituting a considerable improvement over the variety "Mrs. Dupont," as well as over all other varieties of which I am aware.

Asexual reproduction of my new variety by both top cuttings and by underground runners, at Newark, New York, shows that the foregoing characteristics and distinctions come true to form and are established and transmitted through succeeding propagations.

The accompanying drawing shows typical specimens of the new variety, with the flowers and foliage in different stages of development.

The following is a detailed description of the new variety, as observed in fields at Newark, New York, in the latter part of the month of September and in the early afternoon, with color terminology in accordance Ridgway's Color Standards and Nomenclature:

Parentage: An unnamed seedling of "Nita" × an unnamed seedling ("Mrs. Dupont" × another unnamed seedling).

Classification: Decorative type; petals remain flat at the opening, with the center developing and unfolding gradually to a symmetrical full flower.

Growth: Upright; attains a height of from 3 to 3½ feet.

Cold resistance: Winter hardy in northern New York; flowers fairly frost resistant, as determined by comparison with other varieties grown under comparable conditions.

Blooming habit: In Newark, New York, climatic area, date of start of bloom is about the middle of September and makes good showing until frost.

Bud:

Color.—When sepals first divide—Pale Congo Pink, Plate 28. When petals begin to unfurl—Light Congo Pink, Plate 28. When half blown: inside of petals—Flesh Pink, Plate 13, with a light suffusion of Pale Yellow Orange, Plate 3; reverse of petals—White, Plate 53, overcast lightly with Flesh Pink, Plate 13.

Peduncle.—Color—Light Cress Green, Plate 31. strength—strong.

Bloom:

Size.—4 inches to 5½ inches.

Stems.—Stiff.

Form.—Decorative.

Petalage.—Double.

Color.—Center of flower—Flesh Pink, Plate 13, with a suffusion of Pale Yellow Orange, Plate 3. Outer petals—Pale Pinkish Cinnamon, Plate 29, with suffusion of Marguerite Yellow, Plate 30. Base of petals—Light Dull Green Yellow, Plate 17. Inside of petals—Hydrangea Pink, Plate 27, with a suffusion of Light Buff, Plate 15. Reverse of petals—White, overcast lightly with Light Buff, Plate 15.

Petals.—Texture—medium. Form — straight, with slight wavy ends.

Fragrance: Characteristic chrysanthemum.

Plant:

Form.—Upright; compact.

Growth.—Free.

Foliage:

Size.—Medium.

Quantity.—Normal.

Color.—Upper side—Dark Cress Green, Plate 31, with a silvery sheen. Reverse side—Cress Green, Plate 31.

Texture.—Leathery.

I claim:

A new and distinct variety of chrysanthemum plant of the decorative type, substantially as herein shown and described, characterized particularly as to novelty by its upright growth, stiff stems and improved form of plant and size, by its free production of blooms having a general color tonality of Hydrangea Pink suffused with Light Buff, by its healthier growth and improved frost resistance, and by the silvery cast of its foliage over the entire plant.

EUGENE S. BOERNER.

No references cited.